United States Patent
Dunbar (10) Patent No.: US 8,383,682 B2
(45) Date of Patent: Feb. 26, 2013

(54) MIXED LIGAND SURFACE-MODIFIED NANOPARTICLES

(75) Inventor: Timothy D. Dunbar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 285 days.

(21) Appl. No.: 12/746,936

(22) PCT Filed: Dec. 16, 2008

(86) PCT No.: PCT/US2008/086914
§ 371 (c)(1),
(2), (4) Date: Jun. 9, 2010

(87) PCT Pub. No.: WO2009/085721
PCT Pub. Date: Jul. 9, 2009

(65) Prior Publication Data
US 2010/0266697 A1    Oct. 21, 2010

Related U.S. Application Data

(60) Provisional application No. 61/016,048, filed on Dec. 21, 2007, provisional application No. 61/015,990, filed on Dec. 21, 2007.

(51) Int. Cl.
| A61K 31/10 | (2006.01) |
| A61K 31/12 | (2006.01) |
| A61K 31/13 | (2006.01) |
| A61K 31/135 | (2006.01) |
| A61K 31/15 | (2006.01) |
| A61K 31/165 | (2006.01) |

(52) U.S. Cl. ........ 514/617; 514/639; 514/641; 514/646; 514/650; 514/651; 514/652; 514/655; 514/667; 514/673; 514/682; 514/690; 514/691; 514/709; 977/773

(58) Field of Classification Search .................. 514/617, 514/639, 641, 646, 650, 651, 652, 655, 667, 514/673, 682, 690, 691, 709; 977/773
See application file for complete search history.

(56) References Cited

U.S. PATENT DOCUMENTS

| 3,389,170 A | 6/1968 | Habicht et al. |
| 4,047,965 A | 9/1977 | Karst et al. |
| 4,089,996 A | 5/1978 | Lange et al. |
| 4,159,205 A | 6/1979 | Miyahara et al. |
| 4,277,269 A | 7/1981 | Sweeting |
| 4,588,575 A | 5/1986 | David |
| 4,778,671 A | 10/1988 | Wusirika |
| 4,954,462 A | 9/1990 | Wood et al. |
| 5,071,635 A | 12/1991 | Yamanaka et al. |
| 5,635,154 A | 6/1997 | Arai et al. |
| 6,200,680 B1 | 3/2001 | Takeda et al. |
| 6,376,590 B2 | 4/2002 | Kolb et al. |
| 6,387,981 B1 | 5/2002 | Zhang et al. |
| 6,710,091 B1 | 3/2004 | Womelsdorf et al. |
| 2002/0004544 A1 | 1/2002 | Kolb et al. |
| 2003/0175217 A1 | 9/2003 | Kropf et al. |
| 2004/0023824 A1 | 2/2004 | Zuechner et al. |
| 2004/0033270 A1 | 2/2004 | Kropf et al. |
| 2005/0048010 A1 | 3/2005 | Kliss et al. |
| 2008/0286362 A1 | 11/2008 | Baran et al. |

FOREIGN PATENT DOCUMENTS

| EP | 0 317 272 | 5/1989 |
| WF | WO 2009/085721 | 7/2009 |
| WO | WO 02/49684 | 6/2002 |
| WO | WO 2008/079800 | 7/2008 |
| WO | WO 2009/085731 | 7/2009 |
| WO | WO 2009/110945 | 9/2009 |

OTHER PUBLICATIONS

"Carbonyl Compounds I" In Unknown book title, author(s), and publisher, Chapter 17, pp. 670-674, 681-687, and 712, accessed on Jun. 8, 2012 at depa.pquim.unam.mx/amyd/archivero/CarboniloYurkanis_10059.pdf.*
Y. Qi, P. Chen, T. Wang, X. Hu, and S. Zhou, "Fabrication of Self-Assembled PEDOT/PSS-ZnO Nanocables with Diverse Inner Core Sizes Facilitated by Vacuum Conditions," *Macromolecular Rapid Communications* 27, 356-360 (2006).
Z. Hu, P.C. Searson, J.F. Herrera Santos, and G. Oskam, "Influence of the Reactant Concentrations on the Synthesis of ZnO Nanoparticles," *Journal of Colloid and Interface Science* 288, 313-316 (2005).
Silva et al., "Morphology of nanometric size particulate aluminium-doped zinc oxide films," *Colloids and Surfaces*, A: Physicochemical and Engineering Aspects 198-200, 551-558 (2002).
Silva et al., "Aluminium doped zinc oxide films: formation process and optical properties," *Journal of Non-Crystalline Solids* 247, 248-253 (1999).
Silva et al., "Aluminium-doped zinc oxide films prepared by an inorganic sol-gel route," *Science Direct, Thin Solid Films* 449, 86-93 (2004).
Yingqun, "Fabrication of PEDOT/PSS-ZnO nanowire by self-assembly method under vacuum condition," *Chinese Science Bulletin* 50 (20), 2288-2290 (2005).
Venkatachari, et al, Ceram. Eng. Sci. Proc., Preparation of Mullite-Based Fibers by Sol-Gel Processing, 11[9-10] pp. 1512-1525 (1990).
International Search Report PCT/US2008/086914.
Gogotsi, *Nanomaterials Handbook*, CRC Press, Jan. 26, 2006, p. 23.
Meulenkamp, E. A., "Synthesis and Growth of ZnO Nanoparticles," *J. Phys. Chem. B*, 102, 5566-5572 (1998).
Wong, E. M.; Searson, P. C.; Bonevich, J. E. "Growth Kinetics of Nanocrystalline ZnO Particles From Colloidal Suspensions," *J. Phys. Chem. B*, 102, 7770-7775 (1998).
Xiong, H. M.; Liu, D. P.; Chen, J. S.; Xia, Y. Y. "Polyether-Grafted ZnO Nanoparticles With Tunable and Stable Photoluminescence at Room Temperature," *Chem. Mater.* 17, 3062-3064 and S1-S4 (2005).
Tang et al., "Aluminum-doped zinc oxide transparent conductors deposited by the sol-gel process," *Thin Solid Films* 238, 83-87 (1994).

* cited by examiner

*Primary Examiner* — James H. Alstrum-Acevedo
(74) *Attorney, Agent, or Firm* — Lucy C. Weiss (57) ABSTRACT

A composition comprises surface-modified nanoparticles of at least one amphoteric metal oxide or oxyhydroxide. The nanoparticles bear, on at least a portion of their surfaces, a surface modification comprising (i) at least one surface modifier selected from lactate, thiolactate, and mixtures thereof, and (ii) at least one surface modifier selected from halide, nitrate, acetate, carbonate, formate, propionate, sulfate, bromate, perchlorate, tribromoacetate, trichloroacetate, trifluoroacetate, carboxylate comprising from one to about four alkyleneoxy moieties, chlorate, and mixtures thereof.

20 Claims, 1 Drawing Sheet

MIXED LIGAND SURFACE-MODIFIED NANOPARTICLES

STATEMENT OF PRIORITY

This application claims the priority of U.S. Provisional Application Nos. 61/016,048 and 61/015,990, both filed on Dec. 21, 2007, the contents of which are hereby incorporated by reference.

FIELD

This invention relates to compositions comprising surface-modified metal oxide or metal oxyhydroxide nanoparticles and, in another aspect, to articles comprising the compositions.

BACKGROUND

Metal oxides have numerous uses. In particular, zinc oxide is used for diverse purposes including, for example, use as a white pigment, as a catalyst, as a constituent of antibacterial skin-protection ointment, and as an activator for rubber vulcanization. Sunscreens and wood varnishes contain finely divided zinc oxide as an ultraviolet (UV)-absorbing pigment.

Zinc oxide is useful as a UV-absorbing agent because it does not degrade upon prolonged exposure to UV light. When its particle size is less than about 20 nanometers (nm), however, its bandgap shifts to higher energy as its particle size decreases, due to quantum confinement. To maximize the number of UV wavelengths absorbed by zinc oxide, particles having a bandgap as close as possible to the semiconductor's bulk bandgap are desirable. Since the shift from the bandgap of the bulk material is greater the smaller the particle size, crystalline particle diameters of at least about 5 nm generally can be useful. Such particle diameters provide bandgap values relatively close to those of the bulk material, resulting in a relatively broad range of absorbed wavelengths.

Nanoparticles of zinc oxide can be sufficiently small, however, so as to scatter only negligible amounts of visible light. Thus, UV light absorbing, but visible light transparent, composites (for example, transparent organic-inorganic hybrid materials, plastics, paints and coatings) can be made using zinc oxide nanoparticles as a filler. To maintain optical transparency, particle diameters (and the diameters of any agglomerates present) generally should be less than about one-tenth the wavelength of light (for example, below about 30 nm).

The preparation of zinc oxide by both dry and wet processes is known. The classical dry method of burning zinc generates aggregated particles having a broad size distribution. Particularly finely divided zinc oxide is prepared predominantly by wet chemical methods using precipitation processes. Precipitation in aqueous solution generally gives hydroxide- and/or carbonate-containing materials that require thermal conversion to zinc oxide. The thermal post-treatment can have a negative effect on the finely divided nature of the particles, as the particles are subjected during this treatment to sintering processes that can lead to the formation of micrometer ($\mu$m)-sized aggregates. These aggregates can be broken down only incompletely to the primary particles by milling or grinding.

In non-aqueous solutions (or aqueous solutions above the decomposition temperature of zinc hydroxide), zinc oxide can be grown through a simple base precipitation according to the following equation (where X is generally a suitable anion and Y is a suitable cation):

Particle growth takes place through an Ostwald ripening process and is diffusion-dependent. As such, particle growth is rather slow at room temperature if 8 nm or larger diameter particles are desired. Elevating the reaction temperature can speed the process to reasonable rates, but this can simultaneously increase the rate of agglomeration.

Various common zinc salts (for example, zinc acetate) have been used as the starting salt in such non-aqueous precipitation processes. However, such starting salts have generally required the use of dilute solutions to avoid relatively high rates of agglomeration, and zinc oxide grown from such salts has tended to form agglomerates that are unsuitable for applications requiring transparency. In addition, zinc oxide grown from such salts often has not been readily dispersible in water, polar organic solvents, or certain other media due to the nature of its surface modification, and dispersions of the zinc oxide have often lacked long-term stability. Such characteristics have hindered industrial use.

SUMMARY

Thus, we recognize that there is a need for metal oxide or metal oxyhydroxide nanoparticles (particularly, zinc oxide nanoparticles) of desired primary particle sizes that are surface-modified so as to be compatible with (and therefore dispersible in) a variety of media (for example, solvents, polymers, paints, coatings, cosmetic formulations, pharmaceutical formulations, and the like), and/or that can be easily tailored to fit the characteristics of a particular medium (for example, through controlled ligand exchange).

Briefly, in one aspect, this invention provides such a composition, which comprises surface-modified nanoparticles of at least one amphoteric metal oxide or oxyhydroxide (most preferably, zinc oxide). The nanoparticles bear, on at least a portion of their surfaces, a surface modification comprising (i) at least one surface modifier selected from lactate, thiolactate, and mixtures thereof (preferably, lactate), and (ii) at least one surface modifier selected from halide, nitrate, acetate, carbonate, formate, propionate, sulfate, bromate, perchlorate, tribromoacetate, trichloroacetate, trifluoroacetate, carboxylate comprising from one to about four alkyleneoxy moieties, chlorate, and mixtures thereof (preferably, selected from acetate, chloride, and mixtures thereof; more preferably, acetate). Preferably, at least about 25 mole percent of the surface modifiers (or "ligands") of the surface modification are selected from lactate, thiolactate, and mixtures thereof.

It has been discovered that such "mixed ligand-modified" nanoparticles can be controllably ligand-exchanged, due to the differential exchange characteristics of the two types of ligands. Surprisingly, lactate or thiolactate ligands exhibit significantly greater stability and resistance to exchange than the other listed ligands (hereinafter, "exchange ligands"). This can render the surface-modified nanoparticles more stable to agglomeration (than corresponding nanoparticles having only exchange ligands), while allowing for ligand exchange to enhance the compatibility of the nanoparticles with a particular medium (for example, the components of a cosmetic formulation). By varying the ratio of the two types of ligands, the extent of ligand exchange (for example, with a more or less hydrophilic or oleophilic ligand) can be controlled and the surface characteristics of the nanoparticles thereby controllably tailored.

The mixed ligand-modified nanoparticles of the invention can be relatively simply prepared from relatively inexpensive starting compounds. For example, it has been observed that use of a mixture of metal carboxylate salts or metal carboxylate salt precursors (that is, carboxylic acids (or, alternatively, carboxylate salts of non-interfering non-metal cations) and metal salts of non-interfering anions) in a basic precipitation process can minimize or even eliminate agglomeration while allowing for metal oxide or metal oxyhydroxide nanoparticle growth to preferred larger average primary particle sizes (for example, average primary particle diameters above 4-5 nm). This can be especially advantageous for producing zinc oxide nanoparticles (for example, zinc oxide nanoparticles having average primary particle diameters in the range of about 5 nm to about 10 nm or more). Such nanoparticles can be well-suited for use in making UV light absorbing, visible light transparent composites, with the resulting particle size control further enabling a tuning of absorption characteristics.

Thus, in at least preferred embodiments, the composition of the invention can meet the above-mentioned need for metal oxide or metal oxyhydroxide nanoparticles (particularly, zinc oxide nanoparticles) of desired primary particle sizes that are surface-modified so as to be compatible with (and therefore dispersible in) a variety of media, and/or that can be easily tailored to fit the characteristics of a particular medium. The composition can therefore further comprise, for example, at least one carrier material or medium (for example, a material or mixture of materials in the form of a gas, a liquid, a bulk solid, a powder, an oil, a gel, a dispersion, and the like).

In another aspect, this invention also provides an article comprising the composition of the invention.

BRIEF DESCRIPTION OF DRAWING

These and other features, aspects, and advantages of the present invention will become better understood with regard to the following description, appended claims, and accompanying drawing, wherein:

DETAILED DESCRIPTION

Definitions

As used in this patent application:

"agglomeration" means an association of primary particles, which can range from relatively weak (based upon, for example, charge or polarity) to relatively strong (based upon, for example, chemical bonding);

"amphoteric" (in reference to a metal oxide or metal oxyhydroxide) means able to function as both a Bronsted/Lowry acid and base;

"dispersion index" means a parameter equal to the particle size, as determined by dynamic light scattering, of metal oxide or oxyhydroxide nanoparticles in a sol, divided by the primary particle size of the particles as determined by ultraviolet-visible spectroscopy or by x-ray diffraction (dispersion index is a quantitative measure of the degree of agglomeration between the primary particles in a sol; theoretically, the dispersion index for non-agglomerated particles equals 1, with the dispersion index increasing in value as the degree of agglomeration between primary particles increases);

"exchange ligand" means a surface modifier other than lactate or thiolactate, as defined above;

"nanoparticles" means particles having a diameter of less than about 100 nm;

"primary particle size or diameter" means the size or diameter of a non-associated single crystal particle; and "sol" means a dispersion or suspension of colloidal particles in a liquid phase;

"substantially non-agglomerated" (in reference to metal oxide or oxyhydroxide nanoparticles) means having a dispersion index of 1-10 (preferably, 1-5; more preferably, 1-3) (for zinc oxide dispersions, when solvent exchanged with dimethylsulfoxide (DMSO) solvent at a concentration of 0.5 weight percent nanoparticles, based upon the total weight of nanoparticles and solvent).

Preparation of Surface-Modified Nanoparticles

The mixed ligand-modified nanoparticles of the composition of the invention can be prepared by any of a variety of known or hereafter developed particle surface modification methods. Useful methods include those described in, for example, U.S. Patent Application Publication No. 2004/0033270 A1 (Kropf et al.), the descriptions of which are incorporated herein by reference.

For example, metal oxide or oxyhydroxide nanoparticles can be prepared by any method that can provide nanosized particles (for a range of applications, preferably, having average primary particle diameters of 1 nanometer (nm) (more preferably, about 3 nm; most preferably, about 5 nm) to about 50 nm (more preferably, about 30 nm; most preferably, about 20 nm), where any lower limit can be paired with any upper limit of the size range). The nanoparticles can then be dispersed in a liquid medium (for example, alcohol, ether, or a polar aprotic solvent) and optionally any water residues removed. The surface modification agents lactic and/or thiolactic acid and the acid form of one or more of the exchange ligands (preferably, acetic acid, hydrochloric acid, or a mixture thereof) can then be added to the resulting dispersion (preferably, by adding the acid form of the exchange ligand(s) first or by adding all acids simultaneously) and the resulting mixture heated under reflux to a temperature between room temperature and the boiling point of the liquid medium (at atmospheric pressure). Optionally, any resulting water can be removed. The resulting surface-modified nanoparticles can be separated (for example, by filtration or centrifugation), washed, and, optionally, dried.

Preferred preparative methods include those that can provide the desired surface modification while maintaining or producing substantially non-agglomerated nanoparticles. Preferred preparative methods include basic precipitation processes.

For example, a preferred process comprises (a) combining (preferably, in at least one solvent) (1) at least one base and (2) at least one metal carboxylate salt (a salt or a mixture of salts) comprising (i) a metal cation selected from metal cations that form amphoteric metal oxides or oxyhydroxides (most preferably, zinc), (ii) a lactate or thiolactate anion (preferably, a lactate anion), and (iii) an exchange ligand (for example, acetate anion), or, alternatively, metal carboxylate salt precursors comprising (i) at least one metal salt comprising the metal cation and a non-interfering anion (that is, an anion that is not reactive with the base), (ii) lactic or thiolactic acid (preferably, lactic), a lactate or thiolactate salt (preferably, lactate) of a non-interfering, non-metal cation (for example, tetraalkylammonium; preferably, tetramethylammonium), or a mixture thereof, and (iii) the acid form of an exchange ligand (for example, acetic acid or a carboxylic acid comprising from one to about four alkyleneoxy moieties), a salt of the exchange ligand and a non-interfering, non-metal cation, or a mixture thereof; and (b) allowing the base and the metal carboxylate salt(s) or metal carboxylate salt precursors to react (for example, to form a metal oxide or metal oxyhydroxide).

Use of such metal carboxylate salts or metal carboxylate salt precursors in a basic precipitation process can enable the preparation of substantially non-agglomerated metal oxide or metal oxyhydroxide nanoparticles. In addition, the salts or their precursors can enable nanoparticles to be grown to preferred larger average primary particle sizes (for example, average primary particle diameters above 4-5 nm). Preferred embodiments of the process can enable control of average primary particle size by varying, for example, the reaction temperature and/or time.

Bases that can be suitable for use in the preferred process include hydroxyl group-containing basic compounds and mixtures thereof. Useful compounds include sodium hydroxide, potassium hydroxide, ammonium hydroxide, tetramethylammonium hydroxide, and the like, and mixtures thereof. Preferred bases include sodium hydroxide (for example, due to its relatively low cost), tetramethylammonium hydroxide (for example, due to its solubility in a wide variety of organic solvents), and mixtures thereof. Tetramethylammonium hydroxide is more preferred.

The base can be used in solid form (for example, as NaOH or KOH pellets) or in the form of a solution in a polar organic solvent (for example, an alkanol such as methanol). A wide range of concentrations can be useful (for example, tetramethylammonium hydroxide can be used in a commercially available concentration of 25 weight percent in methanol). In a preferred embodiment of the preferred process, the base can be added in solution form to a solution of metal carboxylate salt or metal carboxylate salt precursors. Solvents useful for dissolving the base include acetone, diethylether, alkanols (for example, methanol, ethanol, and isopropanol), dimethylsulfoxide (DMSO), dimethylformamide (DMF), tetrahydrofuran (THF), ethyl acetate, and the like, and mixtures thereof, with alkanols being preferred and methanol more preferred.

The above-described metal carboxylate salt(s) can be used in the preferred process in combination with one or more other salts (for example, salts such as zinc chloride) having only non-interfering anions (as defined below in reference to Formula I). Preferably, at least about 25 mole percent of such a combination, however, will be the above-described metal carboxylate salt(s). If desired, the other salts having non-interfering anions can comprise other metal cations (for example, at levels up to about 10 mole percent, based upon the total number of moles of metal cation), but preferably all metals in the other salts are selected from those that form amphoteric metal oxides or oxyhydroxides.

Metal salts suitable for use in the preferred process include those that comprise (i) a metal cation selected from metal cations that form amphoteric metal oxides or oxyhydroxides and (ii) a lactate or thiolactate anion (or both), and those that comprise (i) such a metal cation and (ii) at least one exchange ligand (for example, acetate anion). Mixed anion salts of such metals and such anions are also useful. Suitable metals include Be, Ti, V, Mn, Cr, Fe, Co, Ni, Al, Zn, Ga, In, Ge, Sn, Pb, As, Sb, Bi, Te, Po, and the like, and mixtures thereof. Preferred cations of such metals include $Be^{+2}$, $Ti^{+4}$, $V^{+4}$, $V^{+5}$, $Mn^{+4}$, $Cr^{+3}$, $Cr^{+4}$, $Fe^{+3}$ $Fe^{+4}$ $Co^{+3}/Co^{+2}$ (mixed oxidation state compound), $Ni^{+3}$, $Ni^{+4}$, $Al^{+3}$, $Zn^{+2}$, $Ga^{+3}$, $In^{+3}$ $Ge^{+2}$, $Sn^{+2}$, $Sn^{+4}$, $Pb^{+2}$, $As^{+3}$ $Sb^{+3}$, $Bi^{+3}$ $Te^{+4}$, $Te^{+4}$, $Po^{+4}$, and the like, and mixtures thereof.

Preferred metals include Ti, V, Mn, Cr, Al, Zn, Ga, In, Sn, Pb, and mixtures thereof. More preferred are Ti, Al, Zn, Ga, In, and mixtures thereof, with Zn being most preferred. If desired, the salts can comprise other metal cations (non-amphoteric) (for example, at levels up to about 10 mole percent, based upon the total number of moles of metal cation), but preferably all metals in the salt(s) are selected from those that form amphoteric metal oxides or oxyhydroxides.

A class of useful metal salts can be represented by the following general formula $$[CH_3CH(Y)COO^-]_m[X^-]_n M^{+(m+n)} \quad (I)$$

wherein each Y is independently —OH or —SH; each X is independently a non-interfering anion (that is, an anion that is not reactive with base); m and n are integers having values such that the sum m+n is equal to the charge of the metal cation, M; and at least about 90 mole percent (preferably, at least about 95 mole percent; more preferably, about 100 mole percent) of M (based upon the total number of moles of metal cation) is selected from Be, Ti, V, Mn, Cr, Fe, Co, Ni, Al, Zn, Ga, In, Ge, Sn, Pb, As, Sb, Bi, Te, Po, and mixtures thereof.

Preferably, Y is —OH; X is an anion selected from halide, nitrate, acetate, carbonate, formate, propionate, sulfate, bromate, perchlorate, tribromoacetate, trichloroacetate, trifluoroacetate, $R'(OR)_xZ(OR)_w(CH_2)_yCOO^-$ (wherein R' is a linear or branched alkyl group having from 1 to about 4 carbon atoms, each R is independently a linear or branched alkylene moiety having from 1 to about 4 carbon atoms, x is an integer of 0 to 4, Z is a divalent organic linking moiety (for example, a moiety non-directionally selected from the group consisting of a covalent bond, —S—, —C(O)O—, —C=C—, and —C(O)NH—, and combinations thereof), w is an integer of 0 to 4 with the proviso that the sum of x+w is an integer of 1 to 4, and y is an integer of 0 to about 3), and chlorate ions, and mixtures thereof (more preferably, selected from chloride, acetate, and mixtures thereof; most preferably, acetate); and/or M is selected from Ti, V, Mn, Cr, Al, Zn, Ga, In, Sn, Pb, and mixtures thereof (more preferably, Ti, Al, Zn, Ga, In, and mixtures thereof; most preferably, zinc).

Representative examples of useful metal salts include metal lactates, metal thiolactates, metal acetates, metal halides (preferably, metal chlorides), metal salts of carboxylates comprising from one to about four alkyleneoxy moieties, metal nitrates, metal propionates, metal carbonates, metal formates, metal sulfates, metal bromates, metal perchlorates, metal tribromoacetates, metal trichloroacetates, metal trifluoroacetates, metal chlorates, and the like (including mixed metal and/or mixed anion salts), and mixtures thereof, where the hierarchy of metal preferences is as set forth above. More preferred metal salts include zinc lactate, zinc thiolactate, zinc acetate, zinc chloride, and mixtures thereof (including mixed anion salts). Zinc lactate (which can be represented as $Zn(Lac)_2$), zinc chloride, and zinc acetate (which can be represented as $Zn(Ac)_2$) are even more preferred, with zinc lactate and zinc acetate being most preferred.

Such metal salts can be obtained from commercial sources or can be prepared from the corresponding metal salts having anions that can be displaced with lactic, thiolactic, and/or other acids (for example, acetic acid). Useful starting metal salts include metal oxynitrates, metal oxychlorides, metal carbonates, metal acetates, metal formates, metal propionates, metal nitrates, metal chlorides, metal oxides, metal hydroxides, metal oxyhydroxides, and the like, and combinations thereof. Many of such salts are commercially available. Metal lactates, metal thiolactates, and metal acetates can be obtained from the reaction of such starting metal salts with lactic, thiolactic, or acetic acid, which are commercially available from Sigma-Aldrich, St. Louis, Mo.

The lactic, thiolactic, and/or other acid (for example, acetic acid or a carboxylic acid comprising from one to about four alkyleneoxy moieties) can be, for example, added to an aqueous solution of a starting metal salt, and then the resulting mixture can be dried, for example, overnight in an oven at about 120° C. Alternatively, a base (for example, sodium hydroxide) can be added to an aqueous solution of starting metal salt to form a precipitate (for example, a metal hydroxide), which can be collected (for example, by filtration), washed (for example, in relatively cold water), and dispersed in water prior to acid addition. The resulting mixture can be reacted by heating, for example, to about 70° C. with overnight stirring. The resulting metal salt can be isolated (for example, by filtration followed by rotary evaporation of the resulting filtrate) and dried (for example, in a vacuum oven). Other orders and manners of combination of the starting metal salt and the acid can be utilized. Stoichiometric amounts of the starting metal salt and the acid generally can be used, although a stoichiometric excess of either reactant can be useful.

Solvents that can be suitable for use in carrying out the preferred process include those in which the metal carboxylate salts or salt precursors and bases can be substantially soluble. Such solvents include polar organic solvents (for example, dimethylsulfoxide (DMSO), dimethylformamide (DMF), acetonitrile, alkanols (for example, methanol, ethanol, isopropanol, 1-methoxy-2-propanol, and the like, and mixtures thereof), N-methyl pyrrolidinone (NMP), water (for example, at temperatures above the zinc hydroxide decomposition temperature when using zinc carboxylate salts), and the like, and mixtures thereof.

Preferred solvents can include DMSO, DMF, acetonitrile, NMP, and mixtures thereof (with DMSO being more preferred), due to the relatively high solubility of metal carboxylates in such solvents. Preferred solvents alternatively can include alkanols (preferably, 1-methoxy-2-propanol), however, due to their ease of removal during purification. Most preferably, the solvent will be capable of dissolving the reactants and products of the process, while keeping the desired metal oxide nanoparticles well-dispersed.

The preferred process can be carried out by combining at least one base and at least one above-described carboxylate-containing metal salt or salt mixture (preferably, in at least one solvent). Alternatively, but less preferably, the process can be carried out by substituting metal carboxylate salt precursors for metal carboxylate salt(s). Such precursors can comprise (i) at least one metal salt comprising a metal cation (selected from metal cations that form amphoteric metal oxides or oxyhydroxides, as described above) and a non-interfering anion (that is, an anion that is not reactive with the base, as described above), (ii) lactic or thiolactic acid, a lactate or thiolactate salt of a non-interfering, non-metal cation (for example, tetraalkylammonium; preferably, tetramethylammonium), or a mixture of any two or more thereof (preferably, lactic acid, lactate salt(s), or a mixture thereof more preferably, lactate salt(s)), and (iii) the acid form of an exchange ligand (for example, acetic acid or a carboxylic acid comprising from one to about four alkyleneoxy moieties), a salt of the exchange ligand and a non-interfering, non-metal cation, or a mixture thereof. A class of useful metal salts can be represented by the following general formula $$M^{+n}[X^-]_n \quad (II)$$

wherein M, X, and n are as defined above for Formula I. In this alternative process, an excess amount of base relative to the amount needed to neutralize all of the carboxylic acid can be utilized to allow reaction of base with the metal present. This alternative process generates one mole of water for each mole of acid neutralized. Water in relatively small amounts can speed the kinetics of growth of ZnO nanoparticles, but the presence of water in relatively larger amounts can cause agglomeration.

Generally, any order and manner of combination of reactants can be utilized, although it can sometimes be preferable to dissolve each reactant separately in solvent prior to combination. Preferably, a substoichiometric amount of base relative to the amount of metal salt(s) or salt precursors (especially when the salt is a zinc carboxylate) can be utilized (for example, to ensure that the resulting metal oxide stays well-dispersed). The mole ratio of lactic or thiolactic acid (or lactate or thiolactate anion) to exchange acid (or exchange anion) can vary over a wide range (depending upon the desired rate of nanoparticle growth, the desired resistance to agglomeration, and the desired amount of exchange ligand for use in ligand exchange processes), but preferably the mole ratio is in the range of 1:3 to 3:1.

Mechanical agitation or stirring can be used, if desired, to facilitate mixing. Optionally, heating can be used to facilitate dissolution, reaction, and/or primary particle size growth. The reactants can be combined in a pressure vessel, if desired (for example, this can be useful for reactions carried out at temperatures above the boiling point of a selected solvent).

To influence, for example, the morphology, magnetic properties, conductivity, light absorption or emission characteristics, and/or the crystallinity of the resulting nanoparticles, various compounds (foreign ions) can be added before, during, or after nanoparticle precipitation. Preferred additive compounds include 2nd-4th main group and transition metal compounds (more preferably, cobalt, gallium, indium, manganese, magnesium, silicon, and aluminum compounds, and mixtures thereof; most preferably, aluminum, gallium, indium, and silicon compounds, and mixtures thereof). Such additive compounds preferably can be added to the reactant combination in dissolved form and/or preferably can be used in an amount from about 0.01 to about 10 mole percent, based on the total number of moles of metal (present, for example, in the form of metal salt).

The resulting surface-modified nanoparticles can be isolated (for example, from a resulting sol) and/or purified by using standard techniques such as decantation (for example, following centrifugation or settling optionally induced by cosolvent addition), filtration, rotary evaporation for solvent removal, dialysis, diafiltration, and the like, and combinations thereof. The characteristics of the resulting product can be evaluated by ultraviolet-visible spectroscopy (absorption characteristics), X-ray diffraction (crystalline particle size, crystalline phase, and particle size distribution), transmission electron microscopy (particle sizes, crystalline phase, and particle size distributions), and dynamic light scattering (degree of agglomeration).

Composition and Articles Comprising the Surface-Modified Nanoparticles

The above-described preparative methods can produce amphoteric metal oxide or oxyhydroxide (most preferably, zinc oxide) nanoparticles bearing, on at least a portion of their surfaces, a surface modification comprising (i) at least one surface modifier selected from lactate, thiolactate, and mixtures thereof (preferably, lactate), and (ii) at least one surface modifier selected from halide, nitrate, acetate, carbonate, formate, propionate, sulfate, bromate, perchlorate, tribromoacetate, trichloroacetate, trifluoroacetate, carboxylate comprising from one to about four alkyleneoxy moieties, chlorate, and mixtures thereof (preferably, selected from acetate, chloride, and mixtures thereof; more preferably, acetate). Preferably, at least about 25 mole percent of the surface modifiers (or "ligands") of the surface modification (more preferably, at least about 40 mole percent; most preferably, at least about 50 mole percent) are selected from lactate, thiolactate, and mixtures thereof.

For use in at least some preferred applications, the surface-modified nanoparticles preferably have average primary particle diameters of 1 nm (more preferably, about 3 nm; most preferably, about 4 nm) to about 20 nanometers (more preferably, about 15 nm; most preferably, about 10 nm) and/or preferably comprise from about 1 weight percent (more preferably, about 2 weight percent; most preferably, about 10 weight percent) to about 40 weight percent surface modifier (more preferably, about 20 weight percent; most preferably, about 15 weight percent), based upon the total weight of the surface-modified nanoparticles (where any lower limit of a range can be paired with any upper limit of the range). The composition of the invention can consist or consist essentially of the surface-modified nanoparticles or can further comprise a carrier material or medium (for example, a material or mixture of materials in the form of a gas, a liquid, a bulk solid, a powder, an oil, a gel, a dispersion, and the like). When the composition is in the form of, for example, a dispersion of the surface-modified nanoparticles in a liquid carrier, free salts of the various ligands can also be present.

The nature (and amount) of the carrier material can vary widely, depending upon the particular application, as is known in the art. The surface-modified nanoparticles can be used, for example, in organic-inorganic hybrid materials (for example, for the UV protection of polymers, paints, coatings, and the like). Preferred embodiments can be useful in making UV light absorbing, visible light transparent composites.

Due to the biocompatibility of the surface modifiers, however, preferred uses for the surface-modified nanoparticles (particularly, zinc oxide) include use in cosmetic formulations and pharmaceutical formulations. The nanoparticles can be used in cosmetic formulations such as sunscreens, antibiotic ointments, oral or dental care compositions, and the like. In such cases, useful carrier materials can include water, water-based liquids, oils, gels, emulsions, microemulsions, dispersions, and the like, and mixtures thereof. The compositions can further comprise, for example, additives commonly used in cosmetics such as fragrances, emulsifiers, thickeners, flavorings, solubilizers, dyes, antibiotics, moisturizers, and the like, and mixtures thereof. The formulation can be borne on a paper or fabric carrier (for example, a woven or non-woven material) to provide a hygiene article (for example, a diaper, tampon, or pantyliner).

A particularly preferred use is in pharmaceutical formulations comprising any of a variety of medicaments. For example, the surface-modified nanoparticles can be used to enhance the mixing and/or delivery of medicaments including antiallergics, analgesics, glucocorticoids, bronchodilators, antihistamines, therapeutic proteins and peptides, antitussives, anginal preparations, antibiotics, anti-inflammatory preparations, diuretics, hormones, and combinations of any two or more of these. Noted categories include beta-agonists, bronchodilators, anticholinergics, anti-leukotrienes, mediator release inhibitors, 5-lipoxyoxygenase inhibitors, and phosphodiesterase inhibitors. The pharmaceutical formulations can further comprise one or more excipients.

Suitable excipients include those listed in the Handbook of Pharmaceutical Excipients (Rowe, et al., APhA Publications, 2003), which include microcrystalline cellulose, dicalcium phosphate, lactose monohydrate (a preferred sugar), mannose, sorbitol, calcium carbonate, starches, and magnesium or zinc stearates. The surface-modified nanoparticles can aid in the preparation of excipient/medicament blends (for example, by reducing mixing times, reducing attrition during processing, and improving the homogeneity of the blends).

The surface-modified nanoparticles can be particularly useful in pharmaceutical inhalation powder formulations (for example, comprising a medicament and optional excipient(s) such as sugar(s) for use in nasal or oral inhalation drug delivery) to enhance the flow characteristics of the powder. The nanoparticles can be present in the formulations in an amount that is at least sufficient to improve the flowability or floodability of the powder relative to corresponding powder that is substantially free of the nanoparticles (for example, the nanoparticles can be used in an amount less than or equal to about 10 weight percent, less than or equal to about 5 weight percent, less than or equal to about 1 weight percent, less than or equal to about 0.1 weight percent, or even less than or equal to about 0.01 weight percent (such as 0.001 weight percent), based upon the total weight of the formulation). Such formulations can generally be prepared by mixing one or more powders (for example, having an average particle size, generally measured as an effective diameter, of less than or equal to about 1,000 microns, more typically less than or equal to about 100 microns) with the surface-modified nanoparticles using any suitable, conventional mixing or blending process.

For example, the surface-modified nanoparticles can be added to an organic solvent so as to form a dispersion, and the powder(s) can be added to the dispersion and the resulting combination stirred or agitated for a period of time to facilitate mixing. The solvent can then be removed by evaporation, with or without the aid of vacuum. Useful solvents include toluene, isopropanol, heptane, hexane, octane, and the like, and mixtures thereof. Preferably, the nanoparticles are zinc oxide nanoparticles, and the solvent is isopropanol. In an alternative method, the surface-modified nanoparticles and the powder(s) can be dry blended, if desired.

The surface-modified nanoparticles can be selected to provide the pharmaceutical inhalation powder formulations with a degree of flowability. If desired, the exchange ligands (for example, acetate surface modifiers) can be ligand exchanged (for example, by adding to a dispersion of the surface-modified nanoparticles, optionally with heating and/or subsequent purification, a hydrophobic or hydrophilic ligand that has a greater affinity for the metal oxide or oxyhydroxide surface than that of the exchange ligand), so that, depending upon the character of the processing solvent or the powder(s), the resulting formulation can exhibit substantially free-flowing properties. The ligand can be described as comprising a headgroup (a part that interacts primarily with the nanoparticle surface) and a tailgroup (a part that interacts with the solvent). Useful headgroups include those that comprise thiol, amine, phosphate, phosphonate, phosphine oxide, sulfate, sulfonate, hydroxamic acid, and/or like moieties. Multiple headgroups can extend from the same tailgroup, as in the case of 2-dodecylsuccinic acid. Useful hydrophobic and/or hydrophilic ligand tailgroups include those that comprise single or multiple alkyl, aryl, oligo-ethylene glycol, and/or like moieties. Multiple tailgroups can extend from the same headgroup, as in the case of triphenylphosphine oxide.

Suitable surface modifiers can thus be selected based upon the nature of the processing solvents and powder(s) used and the properties desired in the resulting formulation. When a processing solvent is hydrophobic, for example, one skilled in the art can select from among various hydrophobic surface modifiers to achieve a surface-modified nanoparticle that is compatible with the hydrophobic solvent; when the processing solvent is hydrophilic, one skilled in the art can select from various hydrophilic surface modifiers; and, when the solvent is a hydrofluorocarbon, one skilled in the art can select from among various compatible surface modifiers; and so forth. The nature of the powder(s) and the desired final properties can also affect the selection of the surface modifiers. The nanoparticle can have a plurality of different surface modifiers (for example, a combination of hydrophilic and hydrophobic modifiers) that combine to provide nanoparticles having a desired set of characteristics. The surface modifiers can generally be selected to provide a statistically averaged, randomly surface-modified nanoparticle.

The surface modifiers can be present on the surface of the nanoparticles in an amount sufficient to provide surface-modified nanoparticles with the properties necessary for compatibility with the powder(s). For example, the surface modifiers can be present in an amount sufficient to form a discontinuous or continuous monolayer on the surface of at least a portion (preferably, a substantial portion) of the nanoparticle.

The resulting pharmaceutical inhalation powder formulations can be stored in a storage article or device (preferably, a dry powder inhaler comprising a mouthpiece and a powder containment system) prior to dosing. This storage article or device can comprise, for example, a reservoir, capsule, blister, or dimpled tape and can be a multi-dose or single-dose device.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise. Solvents and other reagents used were obtained from Sigma-Aldrich Chemical Company, St. Louis, Mo., unless otherwise noted.

Primary Particle Size Determination

The ultraviolet (UV)-visible (Vis) spectrometer used to monitor primary particle sizes was a PerkinElmer™ Lambda 35 instrument (available from PerkinElmer Life and Analytical Sciences, Wellesley, Mass.) with 1 cm path length UV-grade quartz sample cells or cuvettes. A small aliquot of experimental sample was withdrawn from its vial and diluted with organic solvent (for example, 200 proof absolute ethanol, USP grade, Aaper Alcohol and Chemical Co., Shelbyville, Ky.). The diluted sample was then shaken well to mix, and approximately 2.5 mL was transferred to a cuvette for UV-visible spectroscopy. The UV-Vis spectrometer was scanned from 500 to 280 nm, at a rate of 1920 nm per minute, using a slit width set for 1 nm and a data collection interval of 1 nm. The spectrometer was set to change from the visible light lamp to the UV light lamp at 326 nm.

The location of the absorption edge of the sample was determined by differentiating the absorbance versus wavelength curve with respect to wavelength, using the Savitzky-Golay procedure supplied with the spectrometer software, where the width parameter was set to 9. In differentiating the absorbance versus wavelength curve, the spectrometer software calculated the negative of the differentiated absorbance versus wavelength curve, so that a curve with a positive peak was the result. The wavelength of the maximum of this peak was taken to be the absorption edge position, $\lambda'_{max}$. The following equation, described by E. A. Meulenkamp in Journal of Physical Chemistry, B, 102, 5556-5572 (1998), was used to determine the particle diameter (d, in nm) from the absorption edge position ($\lambda'_{max}$, also in nm).

$$d = \{0.017 + [(334.56/\lambda'_{max}) - 0.8904]^{1/2}\} / [(375.64/\lambda'_{max}) - 1]$$

Determining $\lambda'_{max}$ and calculating particle diameter in this manner provided a diameter that corresponded to the mode of the particle size distribution of the sample.

Because light scattering leads to an incorrect measurement of absorbance and therefore an incorrect determination of primary particle size, primary particle sizes were not calculated when samples scattered to an appreciable amount (for example, due to significant agglomeration). This appreciable amount was defined as the absorbance at 400 nm divided by the absorbance at the top of the absorption edge. When this number was greater than 0.2, no primary particle sizes were calculated.

If desired, standard X-ray diffraction (XRD) techniques can be used to determine primary particle size when ultraviolet-visible spectroscopy is insufficient due to such an appreciable amount of particle agglomeration. A sample can be prepared and placed on a zero background specimen holder composed of single crystal quartz by taking an already-prepared sol and placing several drops on the holder and allowing the solvent to evaporate, or by slurrying dried nanoparticles in a low-boiling solvent such as acetone and then placing several drops on the holder and allowing the solvent to evaporate. Reflection geometry data can be collected in the form of a survey scan by use of a PANalytical (Westborough, Mass.) vertical diffractometer, copper K radiation, and proportional detector registry of the scattered radiation. The diffractometer can be fitted with variable incident beam slits, fixed diffracted beam slits, and graphite diffracted beam monochromator. The survey scan can be conducted from 5 to 80 degrees (2) using a 0.04 degree step size and 24 second dwell time. X-ray generator settings of 45 kV and 35 mA can be employed. Observed diffraction peaks can be subjected to profile fitting using a Pearson VII peak shape model, cubic spline background model, and application of JADE X-ray diffraction analysis software (v7.5, Materials Data Incorporated (MDI), Livermore, Calif.). Peak widths can be taken as the full width at half maximum (FWHM) of the $K_{\alpha 1}$ component. Apparent crystallite sizes ($D_{app}$) can be determined using the Scherrer equation (set forth below) and observed peak FWHM values after corrections for instrumental broadening and employing a shape factor of 0.9.

$$D_{app} = K\lambda/\beta \cos(\theta) \text{(result in Å)} \quad \text{Scherrer equation}$$

where
K=0.90 shape factor
$\lambda$=1.540598 Å wavelength Cu $K_{\alpha 1}$
$\beta$=peak FWHM value (in radians) after correction for instrumental broadening
$\theta$=half of the peak position $2\theta$
(*X-ray Diffraction Procedures for Polycrystalline and Amorphous Materials*, Chapter 9, p. 491, Harold P. Klug and Leroy E. Alexander, John Wiley & Sons, Inc., New York (1954); P. Scherrer, *Göttinger Nachrichten*, 2, p. 98 (1918).)

Zinc Oxide Concentration Determination

The concentration of zinc oxide in selected dispersions was determined by measuring the height of the UV-visible absorption edge of the dispersion and multiplying by a reported zinc oxide nanoparticle extinction coefficient times the dilution factor of the dispersion. (An extinction coefficient of 0.135 mg mL$^{-1}$ A$^{-1}$ cm$^{-1}$ has been reported for zinc oxide nanoparticles approximately 4 nm in diameter by Hu et al. in Journal of Colloid and Interface Science, 288, 313-316 (2005), and this number was used in all calculations). The height of the absorption edge was often not clear, since the feature was an edge and not a distinct peak. To reproducibly calculate the absorption edge height and to compensate for absorption edges with varying widths, the following procedure was used.

The $\lambda'_{max}$ of the peak occurring in the $\lambda'$ (differentiated absorbance) curve was determined as described above. The full-width-at-half-maximum (FWHM) of the peak was then determined as follows. A left minimum position of the peak was taken as the differentiated absorbance value of the minimum of the $\lambda'$ curve in the range of between 15 nm and 45 nm lower in wavelength than $\lambda'_{max}$. A right minimum position of the peak was taken as the differentiated absorbance value on the $\lambda'$ curve that was 30 nm greater in wavelength than $\lambda'_{max}$. Left and right halfway points of the peak in the differentiated absorbance curve (points that were halfway from the base of the peak to the maximum of the peak) were determined by averaging the maximum and the respective minimum points. The FWHM was then determined by subtracting the wavelength value of the left halfway point (shorter wavelength) from the wavelength value of the right halfway point (longer wavelength).

After the FWHM was determined, the absorbance value of the absorption edge of the dispersion was calculated. In order to account for baseline offsets in the absorbance curve, the absorption edge was baselined by subtracting the absorbance value of a point at the bottom of the absorption edge from the absorbance value of a point at the top of the absorption edge. The absorbance value of the point at the top of the absorption edge was the absorbance value at a wavelength corresponding to $\lambda'_{max}$ minus 1.3 times the FWHM. The absorbance value of the point at the bottom of the absorption edge was the absorbance value at a wavelength corresponding to $\lambda'_{max}$ plus 1.3 times the FWHM. The final, reported absorbance value for the absorption edge was the result of subtracting the bottom (lower) absorbance value from the top (higher) absorbance value.

Decree of Agglomeration

Dynamic light scattering measurements were made using a Malvern NANOSIZER Nano-ZS, Model Number ZEN-3600, particle size analyzer (available from Malvern Instruments, Malvern, U.K.) and were used to monitor the agglomeration of particles over time. A small (1 g) aliquot was taken from a sample vial in an oil bath and diluted with 1 g dimethylsulfoxide (DMSO). The diluted sample was mixed well and then transferred to a glass cuvette. Light scattering data was recorded with the sample temperature set at 25° C. In transforming the resulting autocorrelation function into particle size, the viscosity ($1.98 \times 10^{-3}$ Pa·s; 1.98 cP) and refractive index (1.479) of dimethylsulfoxide were used. The reported agglomerated particle diameter was based upon an intensity weighted distribution.

Examples 1-3 and Comparative Examples 1 and 2

Zinc lactate (Pfaltz & Bauer, Waterbury, Conn.) was dried in a vacuum oven overnight at 100° C. Thermal gravimetric analysis (TGA) of the zinc lactate was conducted before and after drying. The temperature in the thermal gravimetric analyzer was raised at a rate of 20° C. per minute up to a temperature of 120° C., and this temperature was held for 20 minutes. Before drying in the vacuum oven, the zinc lactate contained 15.7 weight percent water. After drying, the zinc lactate contained 2.4 weight percent water.

Zinc oxide was synthesized using various ratios of zinc lactate ($Zn(Lac)_2$) to zinc acetate ($Zn(Ac)_2$). A 0.52 mmole per gram stock solution of $Zn(Ac)_2$ was prepared by dissolving 2.75 g dry zinc acetate (Alfa Aesar, Ward Hill, Mass., 183.5 g/mole) in 26.35 g dimethylsulfoxide (DMSO, EMD Chemicals, Gibbstown, N.J., OMNISOLV grade). Various amounts of $Zn(Lac)_2$ and DMSO were added to portions of the stock solution to prepare a series of samples as shown in Table 1 below.

TABLE 1

| Example Number | Amount of $Zn(Lac)_2$ (g) | Amount $Zn(Ac)_2$ Stock Solution (g) | Mole Percent $Zn(Lac)_2$ | Mole Percent $Zn(Ac)_2$ |
|---|---|---|---|---|
| C-1 | 0.91 | 0 | 100 | 0 |
| 1 | 0.66 | 1.85 | 74 | 26 |
| 2 | 0.45 | 3.7 | 49 | 51 |
| 3 | 0.23 | 5.55 | 25 | 75 |
| C-2 | 0 | 7.4 | 0 | 100 |

Figure 1:
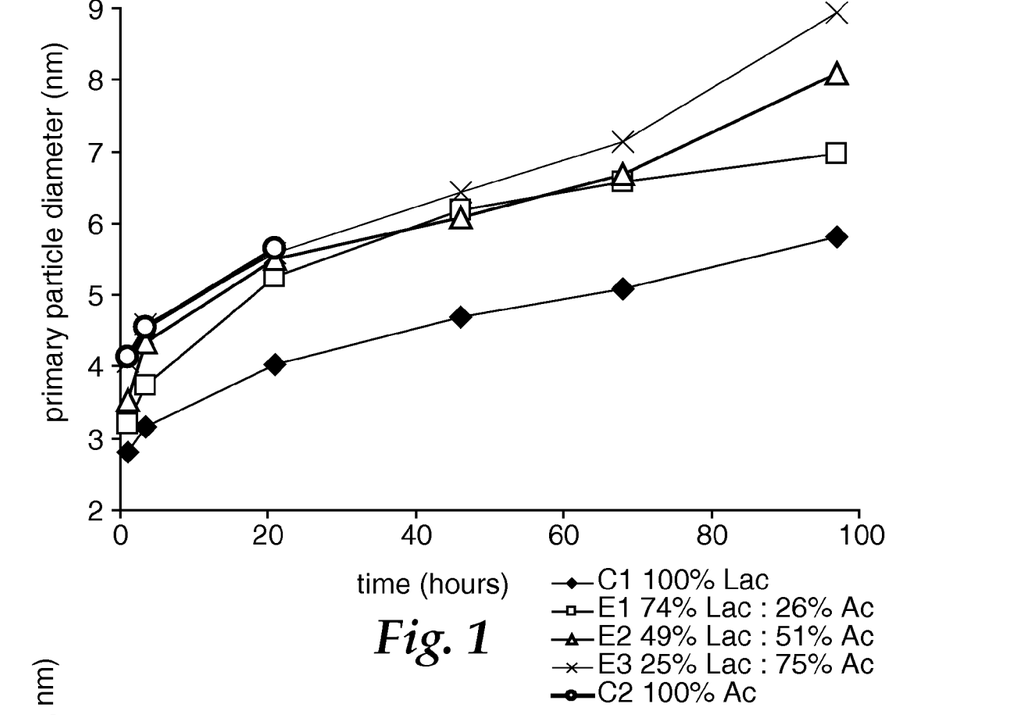
FIG. 1 is a plot of average primary particle diameter versus time for the composition embodiments described in Examples 1-3 and Comparative Examples 1 and 2.
Figure 2:
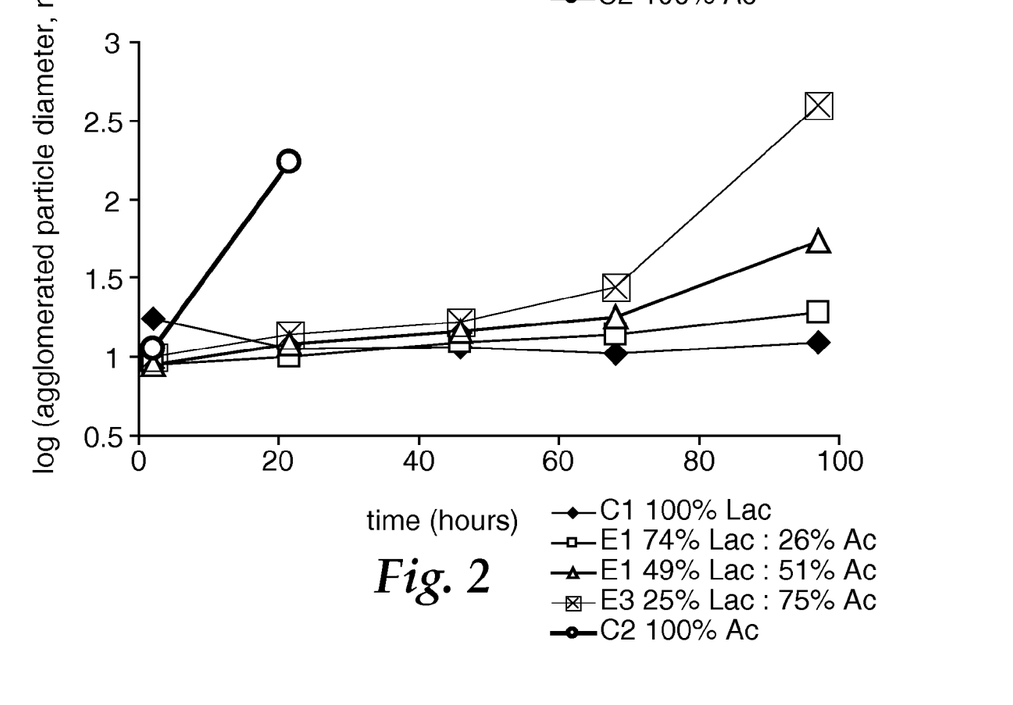
FIG. 2 is a plot of the log of average agglomerated particle diameter versus time for the composition embodiments described in Examples 1-3 and Comparative Examples 1 and 2.

Each sample was placed in a 40 mL vial, to each of which was added 20.3 g DMSO and a magnetic stir bar. Each vial was then placed in an oil bath set to 90° C. To each vial was then added 2.3 g of tetramethylammonium hydroxide (25 percent in methanol, Alfa Aesar, Ward Hill, Mass.). Each of the five samples was expected to contain about 1 percent by weight ZnO nanoparticles. The samples were analyzed by UV-visible spectroscopy (using a 0.5 g aliquot and 24.5 g 200 proof ethanol) and dynamic light scattering at various time intervals. The results are displayed graphically in FIGS. 1 and 2.

Example 4 and Comparative Example 3

Ligand Exchange Comparison of ZnO-[(Lac)(Ac)] (Zinc Oxide Grown from a 1:1 Molar Ratio Mixture of Zinc Acetate and Zinc Lactate) and ZnO-[Lac] (Zinc Oxide Grown from Solely Zinc Lactate)

Preparation of ZnO-[(Lac)(Ac)] Nanoparticle Dispersion

A zinc oxide nanoparticle dispersion was prepared by first dissolving 2.24 g zinc lactate (9.21 mmoles, Pfaltz & Bauer, Waterbury, Conn., dried essentially as described above) and 1.69 anhydrous zinc acetate (9.21 mmoles, Alfa Aesar, Ward Hill, Mass., 183.5 g/mole) in 14.64 g DMSO (EMD Chemicals, Gibbstown, N.J., OMNISOLV grade) that was being heated to 80° C. in a silicone oil heat bath. Then, 11.42 g of tetramethylammonium hydroxide (25 percent by weight in methanol, 31.3 mmoles, Alfa Aesar, Ward Hill, Mass.) was added to the resulting solution dropwise. The resulting growth of zinc oxide particles was monitored using UV-visible spectroscopy. After 1 hour of heating at 80° C., the zinc oxide particles had reached an average size of 5.15 nm. Removing the particle-containing dispersion from the heat bath stopped the particle growth.

5 g of the resulting zinc oxide nanoparticle dispersion was diluted with 5 g of DMSO. 0.33 g of 3-(ethylenediamino) propyl-functionalized silica gel was added to the diluted dispersion, and the resulting mixture was stirred magnetically at room temperature for two days. The silica gel was then removed from the dispersion by filtration through a 37 mm diameter 1 micron glass fiber membrane syringe filter (Pall Life Sciences, East Hills, N.Y., Acrodisc™ #4524T). UV-visible spectroscopy was used to analyze the resulting purified dispersion (150× dilution effected by diluting 0.1 mL in 14.9 mL 200 proof ethanol). Zinc oxide with a diameter of 5.33 nm and a concentration of 21.9 mg zinc oxide per mL was detected.

Preparation of ZnO-[Lac] Nanoparticle Dispersion

A first attempt to dissolve a sufficient amount of dried zinc lactate in DMSO such that it could, upon addition of base, make a zinc oxide dispersion that would be 5 percent by weight zinc oxide, resulted in a solution of zinc lactate in DMSO that quickly gelled and could not be magnetically stirred. Thus, a zinc oxide dispersion that was 5 percent by weight zinc oxide was made in the following manner.

Dried zinc lactate (0.90 g, 3.7 mmoles, Pfaltz & Bauer, Waterbury, Conn., dried essentially as described above) was dissolved in 14.09 g DMSO (EMD Chemicals, Gibbstown, N.J., OMNISOLV grade) that was being heated to 80° C. in a silicone oil heat bath. Fifteen minutes were allowed for the zinc lactate to dissolve. Tetramethylammonium hydroxide (25 percent by weight in methanol, 2.28 g, 6.25 mmoles, Alfa Aesar, Ward Hill, Mass.) was added dropwise to the resulting solution. Fifteen more minutes were allowed for the base to react with the zinc lactate. This cycle of adding zinc lactate, waiting, adding base, and waiting was repeated four more times, so that a total of 18.5 mmoles zinc lactate had been added and 31.3 mmoles base had been added. The resulting growth of zinc oxide particles was monitored using UV-visible spectroscopy. After 26 hours of heating at 80° C., the zinc oxide particles had reached an average size of 5.09 nm. Removing the particle-containing dispersion from the heat bath stopped the particle growth.

5 g of the resulting zinc oxide nanoparticle dispersion was diluted with 5 g of DMSO. 0.33 g of 3-(ethylenediamino)propyl-functionalized silica gel was added to the diluted dispersion, and the resulting mixture was stirred magnetically at room temperature for two days. The silica gel was then removed from the dispersion by filtration through a 37 mm diameter 1 micron glass fiber membrane syringe filter (Pall Life Sciences, East Hills, N.Y., Acrodisc™ #4524T). UV-visible spectroscopy was used to analyze the resulting purified dispersion (150× dilution effected by diluting 0.1 mL in 14.9 mL 200 proof ethanol). Zinc oxide with a diameter of 5.06 nm and a concentration of 24.6 mg zinc oxide per mL was detected.

Ligand Exchange with 1-Dodecanethiol

A solution (hereinafter "Solution A") was created by weighing 0.30 g 1-dodecanethiol (1.5 mmoles) into a glass bottle, adding 24.7 g 1-methoxy-2-propanol, and mixing well. This resulted in a solution that contained 0.06 mmole 1-dodecanethiol per gram of solution.

1 mL of each of the two above-prepared ZnO nanoparticle dispersions was added to 15 mL centrifuge tubes. To the dispersion was added a small stir bar (10 mm×3 mm). The centrifuge tubes were immersed in a silicone oil heat bath that was held at 80° C. To the heated nanoparticle dispersions were added 0.36 g of Solution A, immediately followed by 0.64 mL of 1-methoxy-2-propanol. The resulting mixtures were heated and stirred for 1 hour.

Immediately upon addition of Solution A, the ZnO-[(Lac)(Ac)] dispersion became opaque and white in color, while the ZnO-[Lac] dispersion remained clear. After cooling the mixtures to room temperature, the cooled mixtures were centrifuged for 20 minutes at 3000 revolutions per minute (rpm). The liquid was decanted from each mixture and analyzed by UV-visible spectroscopy for any zinc oxide nanoparticles that did not react (undergo ligand exchange) with the 1-dodecanethiol. Any solids that remained after centrifugation were slurried in 2.9 mL ethanol by first shaking by hand and then magnetic stirring for at least 1 hour. (Essentially no solids remained from the ZnO-[Lac] reaction (undergo ligand exchange) with 1-dodecanethiol.) The resulting ethanol-based slurry was centrifuged for 20 minutes at 3000 rpm. The ethanol was then decanted. Any remaining solids were re-dispersed in 2.9 mL chloroform (EMD Chemicals, Gibbstown, N.J., OMNISOLV grade) by magnetic stirring.

UV-visible spectroscopy was used to analyze the resulting chloroform dispersions by diluting 0.1 mL of each dispersion to 3.0 mL using chloroform (30× dilution factor) in a quartz cuvette. The amounts of zinc oxide that were functionalized with 1-dodecanethiol and dispersed in $CHCl_3$ are shown in Table 2 below for each dispersion, where the height of the zinc oxide absorption edge was determined as described above.

TABLE 2

| Example No. | Starting Nanoparticle Dispersion | Absorption Edge Height (AU) | Dilution Factor | Concentration Of ZnO (mg/mL) | Solution Volume (mL) | Amount of ZnO (mg) |
|---|---|---|---|---|---|---|
| C-3 | ZnO-[Lac] | 0 | 30 | 0 | 2.9 | 0 |
| 4 | ZnO-[(Lac)(Ac)] | 1.809 | 30 | 7.49 | 2.9 | 21.7 |

The amounts of zinc oxide that remained in the DMSO dispersions after reaction (ligand exchange) with 1-dodecanethiol are shown in Table 3 below for each dispersion.

TABLE 3

| Example Number | Starting Nanoparticle Dispersion | Absorption Edge Height (AU) | Dilution Factor | Concentration Of ZnO (mg/mL) | Solution Volume (mL) | Amount of ZnO (mg) |
|---|---|---|---|---|---|---|
| C-3 | ZnO-[Lac] | 0.776 | 100 | 10.71 | 2 | 21.4 |
| 4 | ZnO-[(Lac)(Ac)] | 0 | 100 | 0.00 | 2 | 0.0 |

Thus, when ZnO-[(Lac)(Ac)] was reacted (underwent ligand exchange) with 1-dodecanethiol, the zinc oxide nanoparticles apparently became sufficiently hydrophobic to flocculate from the relatively polar DMSO dispersion. The zinc oxide could be centrifuged out as a solid, slurried with ethanol (to remove any remaining DMSO), centrifuged out as a solid again, and successfully re-dispersed in a relatively much less polar solvent (namely, chloroform).

In contrast, ZnO-[Lac] apparently did not react (undergo ligand exchange) with 1-dodecanethiol sufficiently to become hydrophobic enough to flocculate in DMSO. Consequently, essentially no zinc oxide could be transferred to the chloroform phase.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

I claim:

1. A composition comprising surface-modified nanoparticles of at least one amphoteric metal oxide or oxyhydroxide, said nanoparticles having a diameter of less than 100 nanometers and bearing, on at least a portion of their surfaces, a surface modification comprising (i) at least one surface modifier selected from the group consisting of lactate, thiolactate, and mixtures thereof, and (ii) at least one surface modifier selected from the group consisting of halide, nitrate, acetate, carbonate, formate, propionate, sulfate, bromate, perchlorate, tribromoacetate, trichloroacetate, trifluoroacetate, carboxylate comprising from one to about four alkyleneoxy moieties, chlorate, and mixtures thereof.

2. The composition of claim 1, wherein the metal of said amphoteric metal oxide or oxyhydroxide is selected from the group consisting of Be, Ti, V, Mn, Cr, Fe, Co, Ni, Al, Zn, Ga, In, Ge, Sn, Pb, As, Sb, Bi, Te, and Po, and mixtures thereof.

3. The composition of claim 2, wherein said metal is selected from the group consisting of Ti, V, Mn, Cr, Al, Zn, Ga, In, Sn, Pb, and mixtures thereof.

4. The composition of claim 3, wherein said metal is selected from the group consisting of Ti, Al, Zn, Ga, In, and mixtures thereof.

5. The composition of claim 4, wherein said metal is zinc.

6. The composition of claim 1, wherein at least 25 mole percent of said surface modifiers of said surface modification are selected from the group consisting of lactate, thiolactate, and mixtures thereof.

7. The composition of claim 1, wherein said surface modification comprises lactate.

8. The composition of claim 7, wherein said surface modification comprises at least one surface modifier selected from the group consisting of acetate, chloride, and mixtures thereof.

9. The composition of claim 1, wherein said surface modification comprises at least one surface modifier selected from the group consisting of acetate, chloride, and mixtures thereof.

10. The composition of claim 1, wherein said surface-modified nanoparticles have average primary particle diameters of 1 nm to 50 nm.

11. The composition of claim 1, wherein said surface-modified nanoparticles comprise from 1 weight percent to 40 weight percent of said surface modifiers (i) and (ii), based upon the total weight of said surface-modified nanoparticles.

12. The composition of claim 1, wherein said surface-modified nanoparticles are substantially non-agglomerated.

13. The composition of claim 1, wherein said composition further comprises at least one carrier material.

14. The composition of claim 13, wherein said composition is a pharmaceutical formulation comprising a medicament.

15. The composition of claim 14, wherein said medicament is a powder.

16. An article comprising the composition of claim 13.

17. An article comprising the composition of claim 15, wherein said article is a dry powder inhaler.

18. A composition comprising surface-modified nanoparticles of zinc oxide, said nanoparticles having a diameter of less than 100 nanometers and bearing, on at least a portion of their surfaces, a surface modification comprising (i) lactate, and (ii) at least one surface modifier selected from the group consisting of acetate, chloride, and mixtures thereof.

19. The composition of claim 18, wherein said surface modifier is acetate.

20. The composition of claim 18, wherein said surface-modified nanoparticles are substantially non-agglomerated, have average primary particle diameters of 1 nm to 20 nm, and comprise from 1 weight percent to 40 weight percent of said surface modification, based upon the total weight of said surface-modified nanoparticles.

* * * * *

UNITED STATES PATENT AND TRADEMARK OFFICE
CERTIFICATE OF CORRECTION

PATENT NO. : 8,383,682 B2  
APPLICATION NO. : 12/746936  
DATED : February 26, 2013  
INVENTOR(S) : Timothy Dehaven Dunbar Page 1 of 1

It is certified that error appears in the above-identified patent and that said Letters Patent is hereby corrected as shown below:

In the Specification

Column 5,
Line 61, delete "$Fe^{+3}$ $Fe^{+4}$ $Co^{+3}$" and insert --$Fe^{+3}$, $Fe^{+4}$, $Co^{+3}$--, therefor.

Column 5,
Line 62, delete "$In^{+3}$ $Ge^{+2}$," and insert --$In^{+3}$, $Ge^{+2}$,--, therefor.

Column 5,
Line 63, delete "$As^{+3}$ $Sb^{+3}$, $Bi^{+3}$ $Te^{+4}$,$Te^{+4}$," and insert --$As^{+3}$, $Sb^{+3}$, $Bi^{+3}$, $Te^{+4}$,--, therefor.

Column 7,
Line 55, delete "thereof" and insert --thereof;--, therefor.

Column 9,
Line 59, delete "5-lipoxyoxygenase" and insert --5-lipoxygenase--, therefor.

Column 11,
Line 59, delete "Savitzsky-" and insert --Savitzky- --, therefor.

Signed and Sealed this
Twenty-fourth Day of June, 2014

Michelle K. Lee
*Deputy Director of the United States Patent and Trademark Office*